US009943569B2

(12) United States Patent
Doki et al.

(10) Patent No.: US 9,943,569 B2
(45) Date of Patent: Apr. 17, 2018

(54) METHOD FOR PREVENTING OR REDUCING POSTOPERATIVE PULMONARY COMPLICATIONS

(71) Applicant: OSAKA UNIVERSITY, Suita-shi, Osaka (JP)

(72) Inventors: Yuichiro Doki, Suita (JP); Shuji Takiguchi, Suita (JP); Akihiro Takata, Suita (JP); Yasuhiro Miyazaki, Suita (JP)

(73) Assignee: OSAKA UNIVERSITY, Suita-shi, Osaka (JP)

( * ) Notice: Subject to any disclaimer, the term of this patent is extended or adjusted under 35 U.S.C. 154(b) by 0 days.

(21) Appl. No.: 15/202,952

(22) Filed: Jul. 6, 2016

(65) Prior Publication Data

US 2017/0007674 A1 Jan. 12, 2017

Related U.S. Application Data

(60) Provisional application No. 62/188,973, filed on Jul. 6, 2015.

(51) Int. Cl.
*A61K 38/22* (2006.01)
*A61K 9/00* (2006.01)
*A61K 31/573* (2006.01)

(52) U.S. Cl.
CPC ............ *A61K 38/22* (2013.01); *A61K 9/0019* (2013.01); *A61K 31/573* (2013.01)

(58) Field of Classification Search
CPC .................................................... A61K 38/22
See application file for complete search history.

(56) References Cited

PUBLICATIONS

Garin ("The Human Experience With Ghrelin Administration," J Clin Endocrinol Metab. May 2013; 98(5): 1826-1837).*
Ueno ("In vitro selection of a peptide antagonist of growth hormone secretagogue receptor using cDNA display," PNAS, 2012, vol. 109, No. 28, p. 11121-11126).*
Weijs ("Strategies to reduce pulmonary complications after esophagectomy," World J Gastroenterol Oct. 21, 2013; 19(39): 6509-6514).*
Smithers ("Comparison of the Outcomes Between Open and Minimally Invasive Esophagectomy," Ann Surg 2007;245: 232-240).*
Karzai ("Hypoxemia during One-lung Ventilation," Anesthesiology 2009; 110:1402-11).*
Adachi et al., "Effects of Ghrelin Administration After Total Gastrectomy: A Prospective, Randomized, Placebo-Controlled Phase II Study", Gastroenterology, 2010, vol. 138, pp. 1312-1320.
Akamizu et al., "Separate measurement of plasma levels of acylated and desacyl ghrelin in healthy subjects using a new direct ELISA assay", The Journal of Clinical Endocrinology & Metabolism, Jan. 2005, vol. 90, No. 1, pp. 6-9.
Akamoto et al., "Neutrophil Elastase Inhibitor (Sivelestat) Preserves Antitumor Immunity and Reduces the Inflammatory Mediators Associated with Major Surgery", Surgery Today, 2007, vol. 37, pp. 359-365.
Ando et al., "A Randomized Trial Comparing Postoperative Adjuvant Chemotherapy with Cisplatin and 5-Fluorouracil Versus Preoperative Chemotherapy for Localized Advanced Squamous Cell Carcinoma of the Thoracic Esophagus (JCOG9907)", Annals of Surgical Oncology, 2012, vol. 19, pp. 68-74.
Daly et al., "Esophageal Cancer: Results of an American College of Surgeons Patient Care Evaluation Study", J Am Coll Surg, May 2000, vol. 190, No. 5, pp. 562-572.
Derogar et al., "Influence of Major Postoperative Complications on Health-Related Quality of Life Among Long-Term Survivors of Esophageal Cancer Surgery", Journal of Clinical Oncology, May 10, 2012, vol. 30, No. 14, pp. 1615-1619.
Dindo et al., "Classification of Surgical Complications: A New Proposal With Evaluation in a Cohort of 6336 Patients and Results of a Survey", Annals of Surgery, Aug. 2004, vol. 240, No. 2, pp. 205-213.
Doki et al., "Ghrelin reduction after esophageal substitution and its correlation to postoperative body weight loss in esophageal cancer patients", Surgery, Jun. 2006, vol. 139, No. 6, pp. 797-805.
Enzinger et al., "Esophageal Cancer", The New England Journal of Medicine, 2003, vol. 349, No. 23, pp. 2241-2252.
Hirai et al., "Poor Prognosis in Esophageal Cancer Patients with Postoperative Complications", Surgery Today, 1998, vol. 28, pp. 576-579.
Hiura et al., "Effects of Ghrelin Administration During Chemotherapy With Advanced Esophageal Cancer Patients: A Prospective, Randomized, Placebo-Controlled Phase 2 Study", Cancer, Oct. 1, 2012, vol. 118, pp. 4785-4794.
Kawahara et al., "Prospective randomized controlled study on the effects of perioperative administration of a neutrophil elastase inhibitor to patients undergoing video-assisted thoracoscopic surgery for thoracic esophageal cancer", Diseases of the Esophagus, 2010, vol. 23, pp. 329-339.
Koch et al., "Regulation and prognostic relevance of serum ghrelin concentrations in critical illness and sepsis", Critical Care, 2010, vol. 14:R94, 10 pages.
Kodama et al., "Ghrelin treatment suppresses neutrophil-dominant inflammation in airways of patients with chronic respiratory infection", Pulmonary Pharmacology & Therapeutics, 2008, vol. 21, pp. 774-779.
Konturek et al., "Ghrelin Ameliorates Colonic Inflammation. Role of Nitric Oxide and Sensory Nerves", Journal of Physiology and Pharmacology, 2009, vol. 60, No. 2, pp. 41-47.
Li et al., "Administration of ghrelin improves inflammation, oxidative stress, and apoptosis during and after non-alcoholic fatty liver disease development", Endocrine, 2013, vol. 43, pp. 376-386.
Li et al., "Ghrelin Inhibits Proinflammatory Responses and Nuclear Factor-kappaB Activation in Human Endothelial Cells", Circulation, 2004, vol. 109, pp. 2221-2226.

(Continued)

*Primary Examiner* — Christina Bradley
(74) *Attorney, Agent, or Firm* — Birch, Stewart, Kolasch & Birch, LLP

(57) ABSTRACT

The present invention relates to methods for preventing or reducing the incidence of postoperative pulmonary complications in surgical patients after an esophagectomy. The inventors discovered that the occurrence of postoperative pulmonary complications after an esophagectomy may be reduced through the perioperative administration of ghrelin to surgical patients.

20 Claims, 4 Drawing Sheets

(56) References Cited

PUBLICATIONS

Liu et al., "Ghrelin Inhibits High Glucose-Induced PC12 Cell Apoptosis by Regulating TLR4/NF-kappaB Pathway", Inflammation, Dec. 2013, vol. 36, No. 6, pp. 1286-1294.
Masuda et al., "Ghrelin Stimulates Gastric Acid Secretion and Motility in Rats", Biochemical and Biophysical Research Communications, 2000, vol. 276, pp. 905-908.
Mazess et al., "Dual-energy x-ray absorptiometry for total-body and regional bone-mineral and soft-tissue composition", Am J Clin Nutr, 1990, vol. 51, pp. 1106-1112.
Miki et al., "Ghrelin Treatment of Cachectic Patients with Chronic Obstructive Pulmonary Disease: A Multicenter, Randomized, Double-Blind, Placebo-Controlled Trial", PLoS One, May 2012, vol. 7, Issue 5, e35708, 10 pages.
Morita et al., "Acute lung injury following an esophagectomy for esophageal cancer, with special reference to the clinical factors and cytokine levels of peripheral blood and pleural drainage fluid", Diseases of the Esophagus, 2008, vol. 21, pp. 30-36.
Muckart et al., "American College of Chest Physicians/Society of Critical Care Medicine Consensus Conference definitions of the systemic inflammatory response syndrome and allied disorders in relation to critically injured patients", Crit Care Med, 1997, vol. 25, No. 11, pp. 1789-1795.
Nagaya et al., "Effects of Ghrelin Administration on Left Ventricular Function, Exercise Capacity, and Muscle Wasting in Patients with Chronic Heart Failure", Circulation, 2004, vol. 110, pp. 3674-3679.
Nagaya et al., "Treatment of Cachexia with Ghrelin in Patients with COPD", Chest, Sep. 2005, vol. 128, No. 3, pp. 1187-1193.
Ono et al., "Effects of a Protease Inhibitor on Reduction of Surgical Stress in Esophagectomy", The American Journal of Surgery, Jan. 1999, vol. 177, pp. 78-82.
Opal et al., "Confirmatory interleukin-1 receptor antagonist trial in severe sepsis: A phase III, randomized, double-blind, placebo-controlled, multicenter trial", The Interleukin-1 Receptor Antagonist Sepsis Investigator Group, Crit Care Med, 1997, vol. 25, No. 7, pp. 1115-1124.
Osugi et al., "Video-assisted thoracoscopic esophagectomy and radical lymph node dissection for esophageal cancer", A series of 75 cases, Surgical Endoscopy, 2002, vol. 16, pp. 1588-1593.
Ryugo et al., "Effect of a Polymorphonuclear Elastase Inhibitor (Sivelestat Sodium) on Acute Lung Injury After Cardiopulmonary Bypass: Findings of a Double-Blind Randomized Study", Surgery Today, 2006, vol. 36, pp. 321-326.
Sakamoto et al., "Elevation of Circulating Interleukin 6 after Surgery: Factors Influencing the Serum Level", Cytokine, Mar. 1994, vol. 6, No. 2, pp. 181-186.
Sato et al., "Cytokine Profile of Serum and Bronchoalveolar Lavage Fluids following Thoracic Esophageal Cancer Surgery", European Surgical Research, 2001, vol. 33, pp. 279-284.
Sato et al., "Randomized Study of the Benefits of Preoperative Corticosteroid Administration on the Postoperative Morbidity and Cytokine Response in Patients Undergoing Surgery for Esophageal Cancer", Annals of Surgery, 2002, vol. 236, No. 2, pp. 184-190.
Sato et al., "Use of low dose dopamine, gabexate mesilate and ulinastatin reduces the water balance and pulmonary complication in thoracic esophagectomy patients", Diseases of the Esophagus, 2005, vol. 18, pp. 151-154.
Shimada et al., "Clinical benefits of steroid therapy on surgical stress in patients with esophageal cancer", Surgery, 2000, vol. 128, pp. 791-798.
Shimakawa et al., "Neoadjuvant Chemotherapy (FAP) for Advanced Esophageal Cancer", Anticancer Research, 2008, vol. 28, pp. 2321-2326.
Shintani et al., "Ghrelin, an Endogenous Growth Hormone Secretagogue, Is a Novel Orexigenic Peptide That Antagonizes Leptin Action Through the Activation of Hypothalamic Neuropeptide Y/Y1 Receptor Pathway" Diabetes, Feb. 2001, vol. 50, pp. 227-232.
Shiozaki et al., "Lymph node metastasis along the recurrent nerve chain is an indication for cervical lymph node dissection in thoracic esophageal cancer", Diseases of the Esophagus, 2001,vol. 14, pp. 191-196.
Sjoquist et al., "Survival after neoadjuvant chemotherapy or chemoradiotherapy for resectable oesophageal carcinoma: an updated meta-analysis", Lancet Oncol, Jul. 2011, vol. 12, pp. 681-692.
Sobin et al., "TNM Classification of Malignant Tumours", 7th Edition. New York, NY: Wiley-Liss, Inc, 2009, 332 pages.
Strasser et al., "Safety, tolerability and pharmacokinetics of intravenous ghrelin for cancer-related anorexia/cachexia: a randomised, placebo-controlled, double-blind, double-crossover study", British Journal of Cancer, 2008, vol. 98, pp. 300-308.
Takata et al., "Effects of ghrelin administration on the early post-operative inflammatory response after esophagectomy", Surg Today, 2015, vol. 45, pp. 1025-1031.
Takata et al., "Randomized Phase II Clinical Trial on Invasion Inhibitory Effect of Ghrelin during Perioperative Period of Esophageal Cancer", the 69th General Meeting of the Japanese Society of Gastroenterological Surgery, Jul. 2014 and English translation thereof.
Takata et al., "Randomized Phase II Study of the Anti-inflammatory Effect of Ghrelin During the Postoperative Period of Esophagectomy", Annals of Surgery, Sep. 13, 2014, vol. 00, No. 00, 8 pages.
Tomimaru et al., "Factors Affecting the Prognosis of Patients with Esophageal Cancer Undergoing Salvage Surgery After Definitive Chemoradiotherapy", Journal of Surgical Oncology, 2006, vol. 93, pp. 422-428.
Tsukada et al., "Effect of perioperative steroid therapy on the postoperative course of patients with oesophageal cancer", Digestive and Liver Disease, 2006, vol. 38, pp. 240-244.
Viklund et al., "Risk Factors for Complications After Esophageal Cancer Resection: A Prospective Population-Based Study in Sweden", Annals of Surgery, Feb. 2006, vol. 243, No. 2, pp. 204-211.
Vila et al., "Bacterial Endotoxin Induces Biphasic Changes in Plasma Ghrelin in Healthy Humans", The Journal of Clinical Endocrinology & Metabolism, Oct. 2007, vol. 92, No. 10, pp. 3930-3934.
Wang et al., "Ghrelin protects mice against endotoxemia-induced acute kidney injury", Am J Physiol Renal Physiol, 2009, vol. 297, pp. F1032-F1037.
Wu et al., "Ghrelin Attenuates Sepsis-induced Acute Lung Injury and Mortality in Rats", American Journal of Respiratory and Critrical Care Medicine, 2007, vol. 176, pp. 805-813.
Wu et al., "Ghrelin improves tissue perfusion in severe sepsis via downregulation of endothelin-1", Cardiovascular Research, 2005, vol. 68, pp. 318-326.
Xu et al., "Molecular Mechanisms of Ghrelin-Mediated Endothelial Nitric Oxide Synthase Activation", Endocrinology, Aug. 2008, vol. 149, No. 8, pp. 4183-4192.
Yamamoto et al., "Randomized phase II study of clinical effects of ghrelin after esophagectomy with gastric tube reconstruction", Surgery, 2010, vol. 148, No. 1, pp. 31-38.
Yamamoto et al., "Reduced plasma ghrelin levels on day 1 after esophagectomy: a new predictor of prolonged systemic inflammatory response syndrome", Surg Today, 2013, vol. 43, pp. 48-54.
Yamasaki et al., "Minimally Invasive Esophagectomy for Esophageal Cancer: Comparative Analysis of Open and Hand-Assisted Laparoscopic Abdominal Lymphadenectomy with Gastric Conduit Reconstruction", Journal of Surgical Oncology, 2011, vol. 104, pp. 623-628.
Yamasaki et al., "Multicenter Phase I/II Study of Docetaxel, Cisplatin and Fluorouracil Combination Chemotherapy in Patients with Advanced or Recurrent Squamous Cell Carcinoma of the Esophagus", Oncology, 2011, vol. 80, pp. 307-313.
Zhang et al., "Ghrelin attenuates intestinal ischemia/reperfusion injury in mice by activating the mTOR signaling pathway", International Journal of Molecular Medicine, 2013, vol. 32, pp. 851-859.

\* cited by examiner

FIGURE 2. SIRS duration after esophagectomy for the ghrelin group versus the placebo group.

FIGURE 3. Postoperative changes in CRP (A) and IL-6 levels (B) in the ghrelin and placebo groups. The CRP and IL-6 levels FIGURE 4. Comparison of the time required to attain positive nitrogen balance between the ghrelin group and placebo group.

METHOD FOR PREVENTING OR REDUCING POSTOPERATIVE PULMONARY COMPLICATIONS

CROSS REFERENCE TO RELATED APPLICATIONS

This non-provisional application claims the benefit under 35 U.S.C. § 119(e) to U.S. Provisional Application No. 62/188,973, filed on Jul. 6, 2015, which is hereby expressly incorporated by reference into the present application.

BACKGROUND OF THE INVENTION

1. Field of the Invention

The present invention pertains to methods for preventing or reducing postoperative pulmonary complications in surgical patients following an esophagectomy.

2. Description of the Related Art

Despite the development of multimodal therapies for esophageal cancers, surgery remains the most reliable treatment for advanced esophageal cancers.[1,2] However, esophagectomy is a highly invasive procedure that is associated with significant morbidity (26%-41%) and mortality (4%-10%).[1] Such highly invasive surgery often causes systemic inflammatory response syndrome (SIRS), which is characterized by the overproduction of cytokines and often leads to postoperative complications.[3,4] Moreover, previous studies have shown that acute postoperative complications exert a long-lasting negative influence on quality of life[5] and contribute to poor prognosis after surgical resection.[6]

Several clinical studies have reported that the use of recombinant interleukin (IL)-1 receptor antagonists,[7] polymorphonuclear elastase inhibitors,[8,9] gabexate mesylate,[10,11] and corticosteroids[12-14] can successfully ameliorate the highly inflammatory state after esophagectomy. However, the use of these supportive treatments has not been standardized.

Postoperative pulmonary complications arise due to unfavorable evolution of a disease in the lungs of a surgical patient after an esophagectomy. Postoperative pulmonary complications are, for example, pneumonia (infectious pneumonia) and pulmonary atelectasis.

Ghrelin is a peptide hormone that is an endogenous ligand for the growth hormone (GH)-secretagogue receptor. Ghrelin has several physiological functions in addition to the secretion of GH, including the promotion of the appetite signal[15] and stimulation of gastrointestinal activity.[16] The clinical application of ghrelin has been found to improve the condition of patients with heart failure,[17] pulmonary disease,[18] and cancer cachexia.[19] Moreover, the inventors found that administration of ghrelin led to improvement in oral food intake and body weight loss in patients after total gastrectomy[20] and esophagectomy[21] in addition to improvement in oral food intake and minimization of adverse events in patients who underwent chemotherapy[22] in randomized trials.

In rodent experiments, ghrelin was found to possess another important biological property, the mitigation of proinflammatory cytokine production and attenuation of stress signals,[23] irrespective of nutritional status or eating behavior. In human subjects, patients who underwent esophagectomy exhibited decreases in ghrelin concentration early during surgery, with a nadir on postoperative day (POD) 1. The concentration of ghrelin remained low at about 50% of the preoperative ghrelin level.[24] The inventors also observed that early deterioration of plasma ghrelin was strongly associated with the prolongation of subsequent SIRS duration after esophagectomy with gastric tube reconstruction. These observations suggested that ghrelin may be effective in controlling or preventing inflammation in patients undergoing esophagectomy.[25]

SUMMARY OF THE INVENTION

The inventors hypothesized that exogenous ghrelin may reduce excess cytokine production and SIRS duration after esophagectomy. A clinical randomized trial conducted by the inventors to investigate the safety and efficacy of ghrelin for reducing early postoperative inflammatory responses in patients who underwent esophagectomy confirmed this hypothesis.

The present invention provides methods for preventing or reducing the incidence of pulmonary complications in surgical patients following an esophagectomy. In the methods, an effective amount of ghrelin is administered perioperatively to a surgical patient who undergoes an esophagectomy. The term 'perioperatively' means preoperatively, intraoperatively, or postoperatively in the present invention. Preferably, ghrelin is administered to the surgical patient continuously. The duration of the administration of ghrelin may be 1 to 14 days, 2 to 12 days, 3 to 10 days or 5 to 10 days. Preferably, the duration of the administration of ghrelin is 3 to 10 days, and more preferably, the duration of the administration of ghrelin is 5 to 10 days. In addition, the administration of the ghrelin to the patient may be started preoperatively, intraoperatively, or postoperatively. The administration of the ghrelin to the patient may be started just before the operation, 1 to 20 hours prior to, or 1 to 5 days prior to the operation. The administration of the ghrelin to the patient may be started anywhere between just after an operation to 5 days after an operation, or anywhere between just after an operation to 7 day after an operation. More preferably, administration of the ghrelin to the patient may be started intraoperatively or as soon as possible after an operation. As preferred examples, the administration of the ghrelin to the patient may be started one day before an operation, within 12 hours before an operation, just before an operation, just after an operation, within 12 hours after an operation, within 24 hours after an operation and within 48 hours after an operation.

In other embodiments of the invention, an effective dosage of ghrelin is administered to the surgical patient continuously. Ghrelin is administered at a dosage of from 0.1 to 2.0 μg/kg/h. Preferably, ghrelin is administered at a dosage in the range of from 0.3 to 0.7 μg/kg/h.

In other embodiments of the invention, ghrelin is administered intravenously via a central vein or a peripheral vein. A central vein is, for example, a subclavian vein, a jugular vein, and a femoral vein. Preferably, ghrelin is administered via a subclavian vein.

In related embodiments of the invention, the methods further comprise administering a steroid composition to the surgical patient before administration of ghrelin or during administration of the ghrelin. The steroid composition may include steroids such as methylprednisolone. Preferably, methylprednisolone is administered at a dosage of around 250 mg per body or 10 mg/kg of body weight.

In related embodiments of the invention, the methods may be used to prevent, treat, or control postoperative pulmonary complications in a surgical patient after an esophagectomy with or without one-lung ventilation. Such methods are effective in preventing, treating or controlling postoperative pulmonary complications, which may include, for example, complications that occur due to one-lung ventilation and complications that may occur in a lung that is deflated during the operation. Such methods are effective in preventing, treating or controlling almost all of postoperative pulmonary complications.

DETAILED DESCRIPTION

Figure 1A:
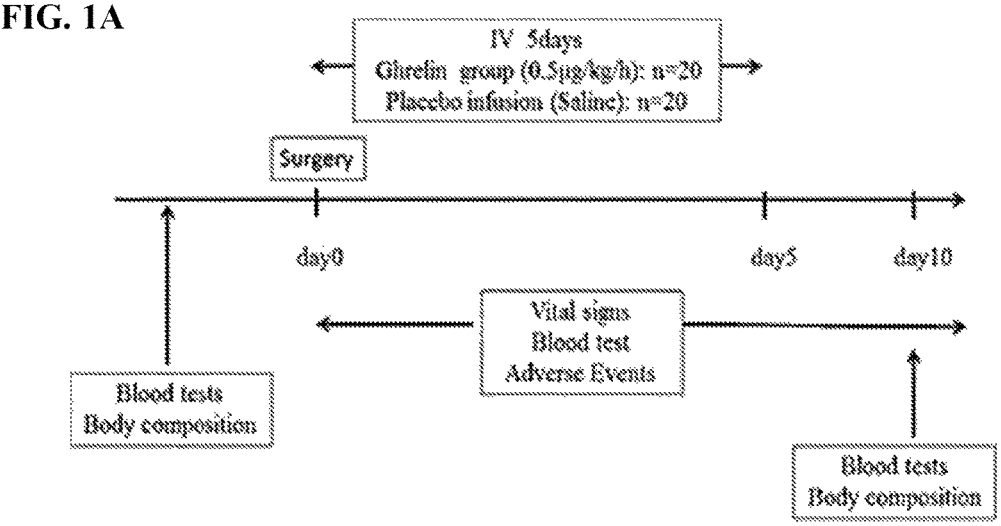
FIG. 1A is a timeline showing the process through the trial.

The present invention is based on the observed effects and safety of ghrelin administration during the perioperative period after major surgery for treatment of esophageal cancer. Surgical treatment of thoracic esophageal cancer is one of the most stressful surgical procedures, and the frequency of postoperative organ failure remains high.[38,39] These stress-induced organ dysfunction states are believed to be induced by excess systemic inflammatory response caused by overproduction of proinflammatory cytokines.[40,41] Perioperative ghrelin administration was effective for inhibiting inflammatory mediators and improving the postoperative clinical course of patients with esophageal cancer.

The anti-inflammatory effects of ghrelin in several animal experimental models have previously been reported, although the underlying mechanism has not been fully elucidated. Ghrelin administration results in various molecular changes and suppresses proinflammatory cytokine production. Ghrelin was found to inhibit NF-κB activation in vascular endothelial cells[23,42,43] and increase NO production in endothelial cells through activation of AMP-activated protein kinase and protein kinase B (Akt).[44] In colonic epithelial cells, ghrelin reduced inflammation by upregulating inducible NO synthase and cyclooxygenase-2 expression.[45] Ghrelin has been shown to downregulate endothelin-1 release from endothelial cells,[46,47] activate the PI3K/Akt/mTOR pathway in nonalcoholic fatty liver disease, and promote activation of the mTOR/p70S6K signaling pathway in intestinal injury.[48,49] These observed effects suggest that the molecular mechanism underlying the anti-inflammatory effects of ghrelin may differ according to the target cells and organs.

In human subjects, several clinical observations have suggested involvement of ghrelin in systemic inflammation. When lipopolysaccharide was injected into healthy volunteers, plasma ghrelin levels decreased and reached a nadir at 5 hours.[50] Another clinical study showed that high ghrelin levels were significantly correlated with favorable prognosis in patients with sepsis in the ICU.[51]

After an esophagectomy plasma ghrelin levels quickly decrease, reaching a nadir of 33% of the preoperative level on POD1, and then gradually recover to 50% of the preoperative level by POD7.[19] Notably, on POD1, plasma ghrelin levels are strongly inversely correlated with systemic inflammation, including postoperative SIRS duration.[24] This phenomenon supports the concept that exogenous ghrelin administration may be helpful for reduction of excess cytokine production and SIRS duration after esophagectomy.

The results of a phase I study of ghrelin administration during the postoperative period after esophagectomy showed that ghrelin administration did not affect fundamental vital signs, such as, blood pressure, heart rate, urine output, and pulmonary and liver function during postoperative intensive care management. In contrast, systemic inflammation tended to be suppressed relative to that of conventional management protocols without ghrelin.

With respect to the mode of ghrelin administration, we found that continuous infusion was better than periodic injection for obtaining better GH secretion (unpublished data). The randomized trial confirmed the reduction of systemic inflammation by ghrelin administration. Exogenous ghrelin successfully decreased SIRS duration and proinflammatory cytokine levels.

In addition, it was noted that administration of ghrelin decreased the incidence of postoperative complications, particularly pulmonary complications, such as, postoperative pneumonia and atelectasis. The effect of ghrelin on respiratory diseases has been reported previously. In patients with chronic obstructive pulmonary disease, ghrelin administration decreased plasma levels of norepinephrine that was secreted by stimulation of the sympathetic nerves.[18] Moreover, in another randomized study, ghrelin administration improved symptoms and respiratory strength of patients with chronic obstructive pulmonary disease.[52] In patients with chronic respiratory infection, ghrelin decreased sputum volume and neutrophil counts in sputum because ghrelin suppressed biosynthesis of TNF-α in mononuclear cells.[53] In this study, the decrease in the incidence of pulmonary complications induced by ghrelin could be attributed to a similar mechanism.

In esophagectomy procedures, whether performed with or without one lung deflated ("one-lung ventilation"), ghrelin may be administered to the surgical patients to prevent or control the development of postoperative pulmonary complications. The deflated lung is often more susceptible to developing complications, such as pneumonia. Thus, the method according to the invention is effective against complications that may occur in a lung that is deflated during an esophagectomy procedure.

Several clinical trials on the application of ghrelin in the treatment of patients with esophageal cancer were conducted. In the course of neoadjuvant chemotherapy, administration of ghrelin stimulated food intake, improved quality of life scores, and minimized adverse events, such as, anorexia and nausea in patients.[22] For patients resuming oral intake after esophagectomy, ghrelin stimulated food intake and attenuated postoperative weight loss and lean body weight loss.[21] Taking the results of these clinical trials together, the inventors developed a comprehensive supportive strategy using ghrelin in the treatment of esophageal cancer. Ghrelin should be useful in each step of multimodal treatments from preoperative chemotherapy to perioperative ICU care and postoperative rehabilitation for oral intake.

The ghrelin to be used in the present invention includes ghrelin and it's derivatives, and composition thereof. The ghrelin is endogenous growth hormone secretagogue, which is peptide having various effects of increasing the intracellular calcium ion concentration, inducing the secretion of growth hormone, enhancing appetite, and reducing inflammation. The suitable ghrelin is that obtained from mammal such as human, rat and porcine. In the present invention, the ghrelin obtained from human is preferably used, and more preferably, the ghrelin obtained from human and having 28 amino acid residues shown below is used.

Most preferably the ghrelin is characterized by a specific structure due to acylation of hydroxyl group at the side chain of the third residue of serine group (S).

Acylated ghrelin (Acyl ghrelin) is active form and non-acylated ghrelin (des-acyl ghrelin) is inactive form. The ghrelin to be used in the present invention may be acylated ghrelin and the other ghrelin. Preferably the contents of acylated ghrelin in the ghrelin are more than 90%, more preferably more than 95%, and most preferably more than 98%.

The modifying hydrophobic group, which is a characteristic of the ghrelin, is not limited to octanoyl (C8) group, and is a residue of fatty acid having 2 to 20, preferably 4 to 12 carbon atoms, such as hexanoyl (C6) group, decanoyl (C10) group or dodecanoyl (C12) group. Further, the modifying hydrophobic group may be a residue of branched or unsaturated fatty acid.

Further, the ghrelin to be used in the present invention include the peptides in which the amino acid sequence is modified by the insertion, addition and deletion of one or more amino acid, and/or the substitution by other amino acid to said amino acid sequence, and is modified chemically if necessary. Further, the ghrelin to be used in the present invention include the peptides in which modifying hydrophobic group is bonded to amino acid chain by ester bond and having same physiologically activity as the ghrelin.

The ghrelin in the present invention includes free form peptides and salts thereof.

The origins and the manufacturing methods of the ghrelin are not limited in the present invention. The ghrelin obtained by chemical process, semichemical process, genetical process or combination process thereof, and extraction from living body can be used in the present invention.

To prepare the ghrelin for administration to patients, synthetic human ghrelin (active form) was obtained from the Peptide Institute Inc (Osaka, Japan) (see, Makino et al., "Synthesis of Ghrelin: Chemical Synthesis and Semisynthesis for Large-Scale Preparation of Modified Peptides" Methods in Enzymology, Volume 514, pp 183-203, 2012; Ishimaru et al., "Stability of the 0-octanoyl group of rat ghrelin during chemical synthesis: Counter-ion-dependent alteration of an ester bond breakage" Letters in Peptide Science, 10: 41-50, 2003.) and treated as described in a previous report.[20-22] Synthetic human ghrelin, which consists of 99.4% acyl ghrelin and 0.6% des-acyl ghrelin, based on analysis by high-performance liquid chromatography, was obtained from Peptide Institute Inc (Osaka, Japan). Ghrelin was dissolved in distilled water containing 3.75% D-mannitol and sterilized by passing the solution through a 0.22 μm filter. Reconstituted ghrelin was stored as 2 mL preparations (each containing 210 μg active ghrelin) in sterile vials at −80° C. until use. Before administration to patients, the ghrelin preparation was diluted to a final volume of 48 mL with saline. The Department of Laboratory for Clinical Investigation, Osaka University Hospital, confirmed that no traces of endotoxin were present in the ghrelin solution and that the solution was pyrogen-free.

The dose of the administered ghrelin was determined based on results from previous studies[20,21,22] (the total dose of ghrelin administration was equal in all studies). The plasma ghrelin concentration was significantly higher than the gut level concentration during administration. Thus, additional studies might be needed to evaluate more suitable ghrelin administration regimens. Finally, ghrelin is not yet commercially available, and its clinical application would have to be validated by supporting evidence in the future.

Forty patients undergoing esophagectomy were randomly assigned to either the ghrelin group (n=20), which received continuous infusion of ghrelin (0.5 μg/kg/h) for 5 days, or the placebo group (n=20), which received pure saline for 5 days. The primary endpoint was SIRS duration. The secondary endpoints were the incidence of postoperative complications, time of a negative nitrogen balance, changes in body weight and composition, and levels of inflammatory markers, including C-reactive protein (CRP) and interleukin-6 (IL-6).

The ghrelin group had a shorter SIRS duration and lower CRP and IL-6 levels than did the placebo group. The incidence of pulmonary complications was lower in the ghrelin group than in the placebo group, whereas other complications did not differ between the groups. Although time of the negative nitrogen balance was shorter in the ghrelin group than in the placebo group, changes in total body weight and lean body weight did not differ significantly.

The inventors found that ghrelin administration during the perioperative period was safe and effective in reducing inflammation and decreasing the incidence of pulmonary complications after esophagectomy. These beneficial effects may be specific to patients undergoing esophagectomy because this procedure is associated with a distinct reduction in ghrelin production, unlike various other surgeries. Thus, ghrelin shows promise as a novel general strategy for postoperative patient management.

EXAMPLES

Study Patients

Forty patients with primary esophageal cancer who underwent esophagectomy were selected to participate in a randomized, placebo-controlled phase II study. The patients were selected based on the following eligibility criteria: (1) thoracic esophageal cancer treated by performing radical esophagectomy with gastric tube reconstruction; (2) age 20 to 75 years; (3) adequate functioning of major organs; (4) no other active malignancies; and (5) provision of written informed consent. The following exclusions criteria were used: (1) preoperative diagnosis of esophageal cancer invasion to the aorta or trachea and other organs; (2) patients with multiple cancer; (3) severe respiratory problems, such as emphysema; (4) patients with prior ischemic heart disease; (5) liver cirrhosis or active hepatitis; (6) renal failure requiring dialysis treatment; (7) poorly controlled diabetes mellitus or disease requiring insulin treatment; (8) consecutive use of steroids; and (9) mental disorder. The patients were randomly divided into a ghrelin group and a placebo group at a 1:1 ratio. The approach for thoracic manipulation (i.e., open or thoracoscopic surgery) was used as the only stratification factor. Group allocation was performed before the initiation of surgery. The study was performed in a double-blind manner, and an independent researcher assessed outcomes.

Operative Procedure and Postoperative Management

All patients underwent preoperative endoscopic examination with biopsy, computed tomography, and combined positron-emission tomography. Clinical staging performed before treatment was based on the criteria of the International Union Against Cancer, seventh edition.[27] Patients diagnosed with esophageal cancer of stage 1B or higher underwent neoadjuvant chemotherapy.[28]

At the initiation of surgery, all patients were injected with methylprednisolone (250 mg) intravenously. With respect to the approach for thoracic manipulation, patients with lymph node involvement in the mediastinum, as demonstrated by pretherapeutic diagnostic imaging, underwent right thoracotomy along the fourth intercostal space. In contrast, patients without lymph node involvement in the mediastinum underwent thoracoscopic surgery in the left lateral decubitus position.[29] Three-field lymphadenectomy was performed as the standard lymph node dissection procedure; prophylactic cervical node dissection was not performed for tumors in the lower two-thirds of the esophagus in the absence of upper mediastinal lymph node metastasis.[30] All abdominal lymphadenectomies and gastric tube reconstructions were performed using a hand-assisted laparoscopic surgical technique with a 7-cm upper abdominal midline incision (through which the surgeon's left hand was inserted) and three 5- to 12-mm-long incisions (through which the trocar tubes were inserted), with the patients in the supine position.[31] A gastric tube with cervical anastomosis was used to repair the defect. The posterior mediastinal route was used for the reconstruction. Enteral nutrition via a jejunostomy tube was not used in any of the enrolled patients.

Postoperative care was standardized and was the same as that described in our previous report.[25] At the end of surgery, all patients were placed on mechanical ventilation and received postoperative care in the intensive care unit (ICU). On POD 1, all patients were weaned off mechanical ventilation and received the same systematic and nutritional care via a central venous infusion. The intravenous infusion consisted of a 2100-mL solution containing 350-g glucose, 115.4-mEq sodium, 54-mEq potassium, and 115.4-mEq chlorine per day. Protein was administered intravenously as needed in the ICU. For analgesia, all patients received 0.375% ropivacaine hydrochloride hydrate passed into the cavity through an epidural catheter inserted at Th7/8 or Th6/7. During the operation, fentanyl and remifentanil hydrochloride were concomitantly used.

End Points and Study Protocol

The primary endpoint of this study was SIRS duration. The secondary endpoints were postoperative complications, serum C-reactive protein (CRP) and IL-6 levels, time required to attain a positive nitrogen balance, and changes in body weight and body composition. Postoperative complications were defined as adverse events caused by surgery. The study design is summarized in FIG. 1A. Patients received an intravenous continuous infusion of ghrelin (0.5 µg/kg/h) or placebo (pure saline) for 5 days postoperatively. Ghrelin was diluted to a final volume of 48 mL with saline, and the solution was administered at a rate of 2 mL/h by using an infusion pump through a central venous catheter inserted into the right subclavian vein. The same amount of ghrelin was administered via intravenous infusion during the 5 days of treatment; the dose was calculated on the basis of body weight on the day before surgery. Patients in the placebo group received the corresponding infusion containing pure saline using same procedure.

Blood sampling was performed at the following 7 time points: before surgery; 2 hours after initiation of surgery (during thoracotomy); 4 hours after initiation of surgery (during laparotomy); and on PODs 1, 3, 7, and 10. Complete blood count was performed every day for at least 10 PODs. If the leukocyte count was not within the normal range on POD10, complete blood counts were performed daily until it was within the normal range for 3 consecutive days. SIRS was diagnosed according to the criteria proposed by the American College of Chest Physicians/Society of Critical Care Medicine Consensus Conference[32] and when 2 or more of the following criteria were present: (1) body temperature less than 36° C. or more than 38° C.; (2) heart rate more than 90 beats per minute; (3) tachypnea with more than 20 breaths per minute or an arterial partial pressure of carbon dioxide less than 32 mm Hg; and (4) white blood cell count less than 4000 cells/mm$^3$, >12,000 cells/mm$^3$, or an immature (band) form more than 10%. Postoperative complications were evaluated according to the Clavien-Dindo classification.[33] Grade I required no treatment, grade II required medical therapy, grade Ma required interventions but not general anesthesia, grade Mb required general anesthesia, grade IV represented life-threatening states that required intensive care, and grade V represented death.

Measurements of Plasma Ghrelin and Serum IL-6 Levels

Sampled blood was immediately transferred into a chilled glass tube containing disodium ethylenediaminetetraacetic acid for plasma sampling or a separating agent for serum sampling, and the samples were then centrifuged at 4° C. Plasma samples were mixed with a 10% volume of 1 N HCl and stored at −80° C. Serum samples were directly stored at −80° C. Sandwich-type enzyme immunoassay kits were used to measure levels of plasma active ghrelin, des-acyl ghrelin, and serum IL-6 according to the manufacturers' protocols (for ghrelin: Mitsubishi Kagaku Iatron, Inc, Tokyo, Japan; for IL-6: R&D Systems, Minneapolis, Minn.). Total plasma ghrelin levels were calculated as the active ghrelin level plus the des-acyl ghrelin level.[34] An Access 2 kit, a chemiluminescent enzyme immunoassay (Beckman Coulter, Inc, Brea, Calif.), was used to measure serum GH levels.

Dual-Energy X-Ray Absorptiometry

Dual-energy X-ray absorptiometry (Hologic QDR-2000; Hologic Inc, Waltham, Mass.) was used to assess total body composition, including lean body weight and fat body weight, of all participants.[35] These measurements were performed preoperatively and 10 days postoperatively with the subject in the supine position.

Sample Size and Statistical Analysis

Based on observations in previous studies, SIRS duration in the placebo group was anticipated to be 4.0±2.0 days.[25] The power calculation was based on a 75% reduction in SIRS duration with ghrelin administration, with a power of 80% and a value of 5%, which required at least 16 patients per study group. Assuming that approximately 20% of the patients in each group would not complete the study, the initial proposal aimed to recruit 20 patients to each group.

Continuous variables are expressed as means±standard deviations unless otherwise stated. The Student t test, Mann-Whitney U test, and λ2 test or multivariate analysis of variance test were used to calculate statistical differences between the groups. Statistical significance was set at $P<0.05$. JMP (version 10.0) software (SAS Institute, Cary, N.C.) was used to perform all calculations.

Results

Patients' Characteristics

Figure 1B:
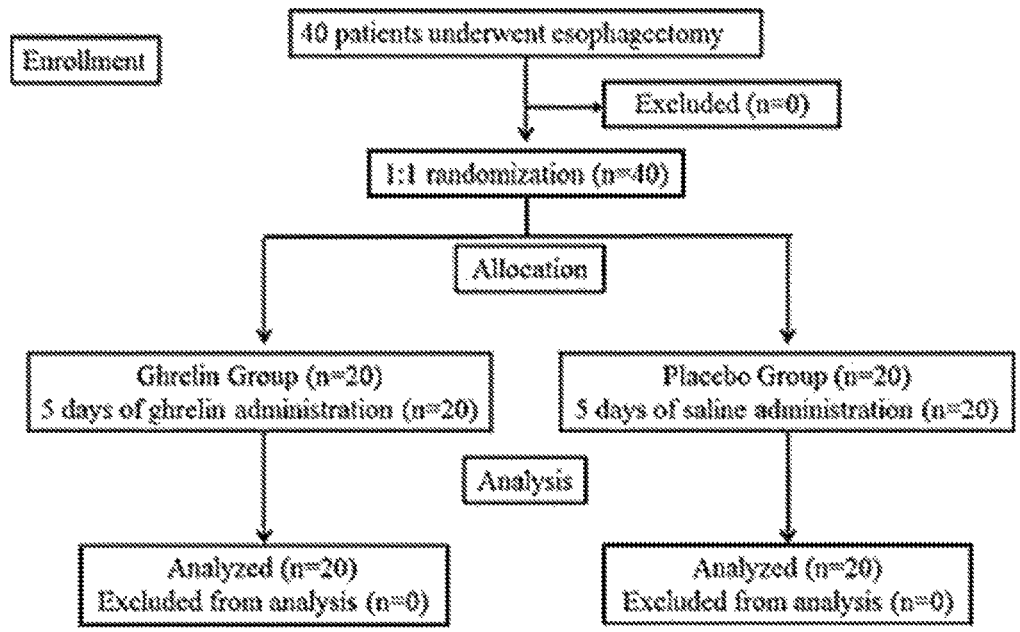
FIG. 1B is a flow diagram illustrating the study protocol.

The study flow diagram is summarized in FIG. 1B. In total, 40 enrolled patients were randomized into either the ghrelin group (20 patients) or the placebo group (20 patients). All patients received the planned dose of ghrelin or placebo during the planned period. No adverse events attributable to ghrelin administration were observed during the study period, and all patients were able to undergo evaluation. Table 1 lists the demographic and clinical characteristics of all patients. Most patients showed an advanced clinical stage, low body weight, and had received neoadjuvant chemotherapy. Regarding neoadjuvant chemotherapy, we used the following 4 different regimens: 5-fluorouracil plus cisplatin plus doxorubicin (n=6),[36] 5-fluorouracil plus cisplatin plus docetaxel (n=29),[37] 5-fluorouracil plus cisplatin (n=1), and cisplatin plus irinotecan (n=1). No significant differences were observed in background characteristics, including age, sex, body mass index, localization of cancer, clinical cancer staging, and preoperative therapy between the 2 groups.

TABLE 1

Patient Characteristics

| Characteristics | Study Group | | |
|---|---|---|---|
| | Ghrelin Group | Placebo Group | P |
| Age, yrs | 65.0 ± 6.5 | 65.8 ± 6.0 | 0.70 |
| Sex (male/female) | 19/1 | 18/2 | 0.55 |
| BMI, kg/m$^2$ | 21.6 ± 3.0 | 21.2 ± 2.5 | 0.62 |
| Tumor localization | | | |
| Upper/middle/lower | 3/9/8 | 2/11/7 | 0.79 |
| Clinical stage I/II/III/IV | 2/7/6/5 | 3/7/7/3 | 0.86 |
| Preoperative therapy* | | | |
| None/ACF/DCF/other | 1/3/15/1 | 2/3/14/1 | 0.95 |
| Lymphadenectomy 2-field/3-field | 8/12 | 9/11 | 0.75 |
| Thoracic surgical approach | | | |
| Thoracoscopic surgery/open surgery | 9/11 | 9/11 | 1.00 |
| Operating time, min | 420.1 ± 40.5 | 432.4 ± 59.1 | 0.66 |
| Blood loss, mL | 463.5 ± 227.7 | 483.8 ± 238.8 | 0.72 |

*ACF, 5-fluorouracil plus cisplatin plus doxorubicia; DCF, 5-fluorouracil plus cisplatin plus docetaxal.

Concentration of Ghrelin

The ghrelin group had significantly higher concentrations of ghrelin than did the placebo group. Before ghrelin administration, the concentration of ghrelin did not differ significantly between both groups (106.6±76.8 vs 131.7±101.3 fmol/mL, respectively; P=0.31). In the ghrelin group, the concentration of ghrelin increased shortly after the start of the injection. In the placebo group, the concentration of ghrelin decreased (the ghrelin concentrations at the following time points in the ghrelin and placebo groups were, respectively, 2 hours after the start of injection, 743.3±191.1 vs 99.9±191.1 fmol/mL; P<0.0001; 4 hours after the start of injection, 710.5±145.7 vs 97.1±62.4 fmol/mL; P<0.0001). During the infusion, the concentration of ghrelin was maintained in the ghrelin group, but the ghrelin concentration reached a minimum at POD1 and remained low in the placebo group (the ghrelin concentrations at the following time points in the ghrelin and placebo groups were, respectively, POD1, 749.2±142.8 vs 57.6±34.2 fmol/mL, P<0.0001; POD3, 737.1±198.5 vs 64.8±46.1 fmol/mL, P<0.0001). After administration of ghrelin, the plasma ghrelin concentrations were similar between both groups (the ghrelin concentrations at the following time points in the ghrelin and placebo groups were, respectively, POD7, 60.2±34.1 vs 63.0±33.3 fmol/mL, P=0.78; POD10, 63.0±31.0 vs 77.0±45.5 fmol/mL, P=0.38).

Figure 2:
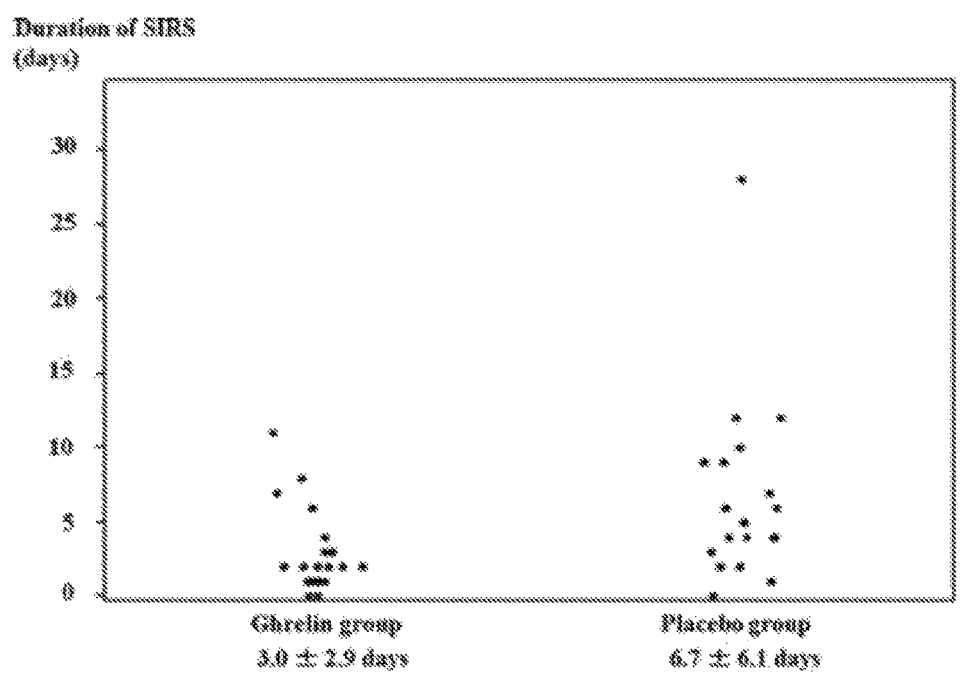
FIG. 2 is a graph showing SIRS duration after esophagectomy for ghrelin group versus placebo group.

Effects of Ghrelin Administration on SIRS Duration and Postoperative Complications To examine the effects of ghrelin administration, we compared the SIRS duration and postoperative complications (Table 2). The SIRS duration was significantly shorter in the ghrelin group than in the placebo group (FIG. 2) (3.0±2.9 vs 6.7±6.1 days, respectively; P=0.0062).

TABLE 2

Postoperative Complications According to the Clavien-Dindo Classification (Version 2.0)

| | Ghrelin Group | Placebo Group | P |
|---|---|---|---|
| Postoperative complication | | | |
| Arrhythmia | | | 0.35 |
| Grade 0 | 19 | 17 | |
| Grade I, II | 1 | 1 | |
| Grade III, IV | 0 | 2 | |
| Lymphorrhea | | | |
| Grade 0 | 20 | 18 | 0.15 |
| Grade I, II | 0 | 2 | |
| Grade III, IV | 0 | 0 | |
| Pneumonia, atelectasis | | | |
| Grade 0 | 14 | 6 | 0.016 |
| Grade I, II | 4 | 5 | |
| Grade III, IV | 2 | 9 | |
| Recurrent nerve paralysis | | | |
| Grade 0 | 18 | 15 | 0.21 |
| Grade I, II | 2 | 5 | |
| Grade III, IV | 0 | 0 | |
| Wound infection | | | |
| Grade 0 | 19 | 17 | 0.49 |
| Grade I, II | 1 | 2 | |
| Grade III, IV | 0 | 1 | |
| Anastomotic leak | | | |
| Grade 0 | 19 | 19 | 0.37 |
| Grade I, II | 1 | 0 | |
| Grade III, IV | 0 | 1 | |
| Bleeding | | | |
| Grade 0 | 20 | 20 | 1.00 |
| Grade I, II | 0 | 0 | |
| Grade III, IV | 0 | 0 | |

Postoperative complications of higher than grade 1 according to the Clavien-Dindo classification were reported in 27 patients (67.5%), including 10 (50%) in the ghrelin group and 17 (85%) in the placebo group. The incidence of complications was significantly lower in the ghrelin group than in the placebo group (P=0.018). In particular, the incidence of pulmonary complications, including postoperative pneumonia and atelectasis, was significantly lower in the ghrelin group than in the placebo group (P=0.016). However, the rates of recurrent nerve paralysis, a complication that had a powerful effect on pulmonary complications or anastomotic leakage resulting from the surgical technique itself, were similar in both groups.

Effects of Ghrelin Administration on Acute-Phase Parameters

Figure 3:
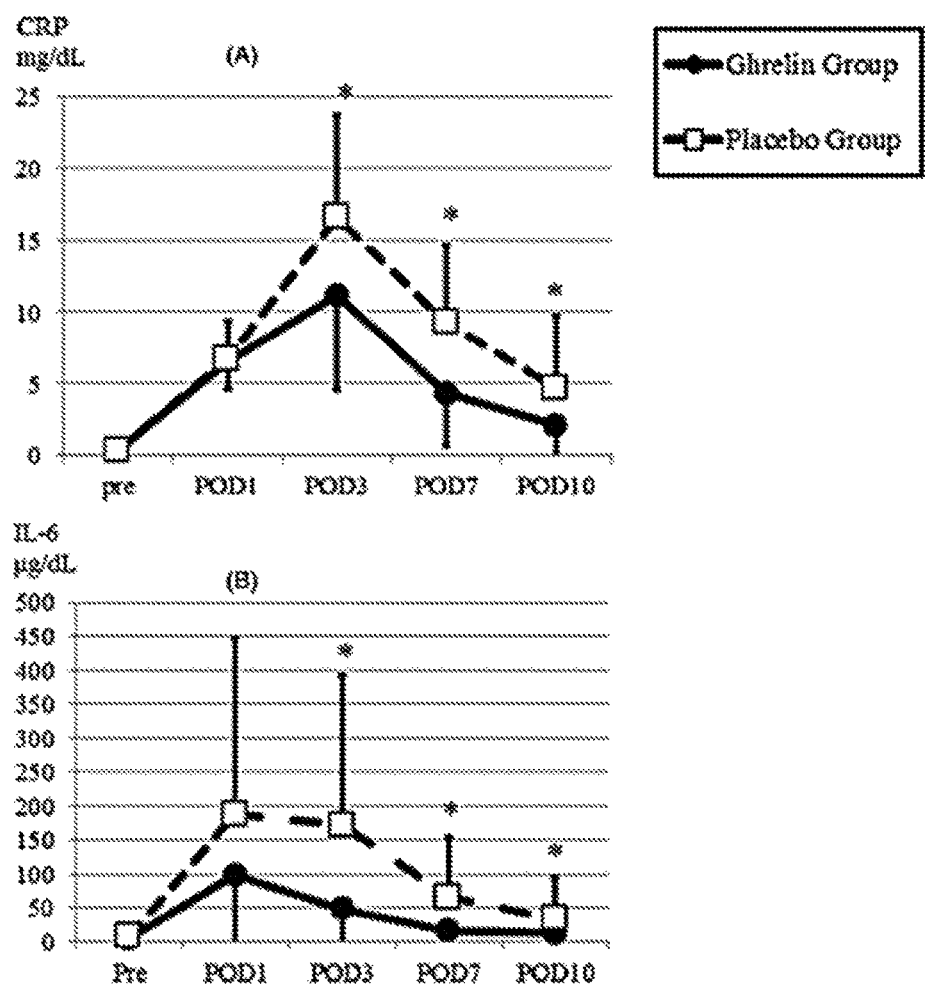
FIG. 3 is a graph showing postoperative changes in CRP (A) and IL-6 levels (B) in the ghrelin and placebo groups. The CRP and IL-6 levels were measured preoperatively, 2 hours after initiation of surgery, and on postoperative days 1, 3, 7, and 10.

To assess changes in the acute-phase parameters, the postoperative changes in serum IL-6 and CRP levels were compared between the 2 groups (Table 3, FIG. 3). Lower CRP and IL-6 levels were observed in the ghrelin group than in the placebo group (P=0.0064 and P=0.028, respectively, by multivariate analysis of variance tests). The postoperative increases in the serum CRP and IL-6 levels relative to the preoperative levels were similar between the groups at POD1, whereas the serum CRP levels were significantly lower in the ghrelin group than in the placebo group at POD3 (11.1±6.6 vs 16.6±7.1 mg/dL, respectively; P=0.0066; FIG. 3A), POD7 (4.3±3.6 vs 9.2±5.4 mg/dL, respectively; P=0.0026; FIG. 3A), and POD10 (2.1±2.3 vs 4.7±5.0 mg/dL, respectively; P=0.0087; FIG. 3A); serum IL-6 levels followed the same trend at POD3 (43.1±47.1 vs 180.0±216.3 pg/mL, respectively; P=0.0002; FIG. 3B), POD7 (15.3±11.3 vs 65.9±88.0 pg/dL, respectively; P=0.0060; FIG. 3A), and POD10 (14.3±17.9 vs 33.6±61.5 pg/dL, respectively; P=0.047; FIG. 3A).

TABLE 3

Postoperative Change in Serum CRP and IL-6

|  | Ghrelin Group (n = 20) | Placebo Group (n = 20) | P |
|---|---|---|---|
| CRP, mg/dL |  |  |  |
| Preoperative | 0.3 ± 0.5 | 0.3 ± 0.3 | 0.48 |
| POD1 | 6.6 ± 2.0 | 6.7 ± 2.6 | 0.95 |
| POD3 | 11.1 ± 6.6 | 16.6 ± 7.1 | 0.0066 |
| POD7 | 4.3 ± 3.6 | 9.2 ± 5.4 | 0.0026 |
| POD10 | 2.1 ± 2.3 | 4.7 ± 5.0 | 0.0087 |
| IL-6, pg/mL |  |  |  |
| Preoperative | 4.3 ± 4.8 | 7.7 ± 17.5 | 0.35 |
| POD1 | 95.2 ± 131.0 | 194.1 ± 257.2 | 0.31 |
| POD3 | 43.1 ± 47.1 | 179.7 ± 216.3 | 0.0002 |
| POD7 | 15.3 ± 11.3 | 65.9 ± 88.0 | 0.006 |
| POD10 | 14.2 ± 17.9 | 33.6 ± 61.5 | 0.047 |

Effects of Ghrelin Administration on the Results of Hematological Examination and Nutritional Status

TABLE 4

Results of Laboratory Tests, Nutrition Status, and Hormone Assays on Preoperative Day and Postoperative Day (POD7)

|  | Preoperative | | | Postoperative | | |
|---|---|---|---|---|---|---|
|  | Ghrelin Group | Placebo Group | P | Ghrelin Group | Placebo Group | P |
| Hemoglobin, g/dL | 11.3 ± 1.5 | 10.9 ± 1.2 | 0.25 | 10.1 ± 1.3 | 9.6 ± 1.3 | 0.29 |
| Leukocytes/mm | 5472 ± 1970 | 5494 ± 1808 | 0.86 | 9068 ± 2633 | 10153 ± 2659 | 0.17 |
| Lymphocytes/mm | 1644 ± 585 | 1817 ± 555 | 0.44 | 1380 ± 495 | 1195 ± 559 | 1.00 |
| Blood urea nitrogen, mg/dL | 15.1 ± 4.7 | 15.6 ± 4.7 | 0.86 | 19.3 ± 6.8 | 16.3 ± 5.6 | 0.082 |
| Creatinine | 0.88 ± 0.21 | 0.90 ± 0.19 | 0.78 | 0.77 ± 0.19 | 0.72 ± 0.21 | 0.23 |
| Asparate aminotransferase, IU/L | 20.2 ± 7.2 | 20.9 ± 6.3 | 0.68 | 34.0 ± 15.9 | 37.2 ± 22.8 | 1.00 |
| Alanine aminotransferase, IU/L | 18.3 ± 14.1 | 15.0 ± 5.9 | 0.96 | 40.6 ± 24.6 | 44.2 ± 31.2 | 0.99 |
| Total bilirubin (mg/dL) | 0.58 ± 0.20 | 0.50 ± 0.26 | 0.24 | 1.25 ± 0.80 | 1.17 ± 0.71 | 0.69 |
| Choline esterase, IU/L | 263.5 ± 83.8 | 281.9 ± 91.1 | 0.90 | 154.1 ± 50.7 | 141.5 ± 46.0 | 0.46 |
| Total protein, g/dL | 6.44 ± 0.59 | 6.22 ± 0.51 | 0.31 | 5.66 ± 0.70 | 4.45 ± 0.51 | 0.30 |
| Albumin, g/dL | 3.78 ± 0.50 | 3.64 ± 0.31 | 0.18 | 2.99 ± 0.45 | 2.95 ± 0.36 | 0.67 |
| Transthyretin, mg/dL | 28.8 ± 9.1 | 26.7 ± 6.7 | 0.45 | 20.1 ± 6.7 | 14.1 ± 5.5 | 0.0083 |
| Retinol binding protein, mg/dL | 4.86 ± 1.71 | 4.76 ± 1.40 | 0.63 | 3.63 ± 1.56 | 2.59 ± 1.15 | 0.022 |
| Transferrin, mg/dL | 198.1 ± 30.8 | 198.8 ± 27.6 | 0.97 | 146.4 ± 35.3 | 125.2 ± 32.6 | 0.031 |
| Total ghrelin, imol/mL | 106.6 ± 76.8 | 131.7 ± 301.3 | 0.31 | 60.2 ± 34.1 | 63.0 ± 33.3 | 0.78 |
| Growth hormone, ng/mL | 0.51 ± 0.54 | 0.65 ± 0.92 | 0.88 | 1.08 ± 1.16 | 1.04 ± 1.15 | 0.56 |

Figure 4:
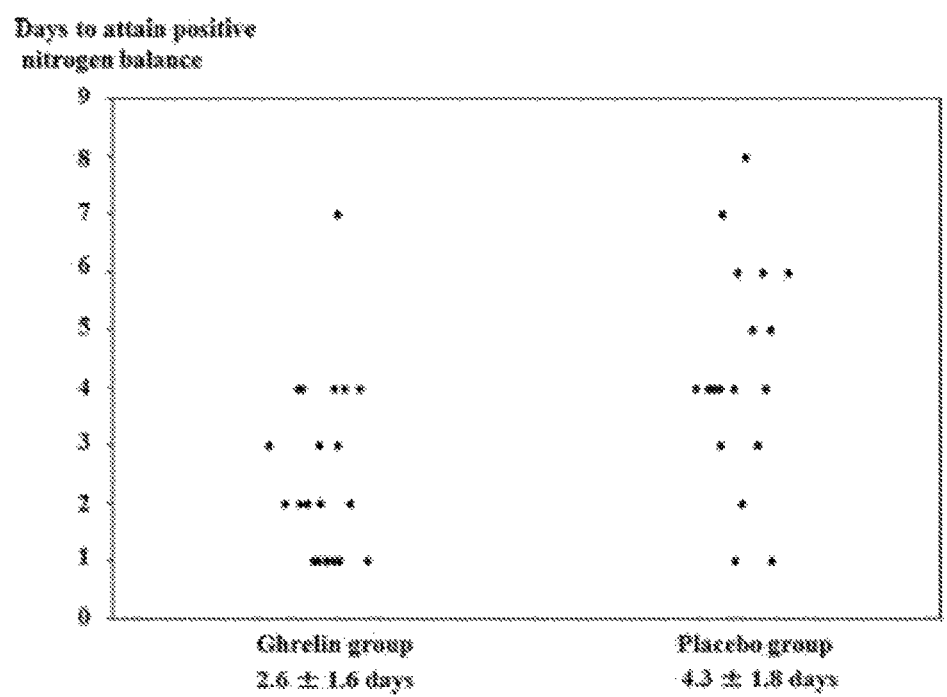
FIG. 4 is a graph showing a comparison of the time required to attain positive nitrogen balance between the ghrelin group and placebo group.

Table 4 shows the results of preoperative and POD7 blood tests in the ghrelin and placebo groups. No significant differences were observed in the results of preoperative hematological examination. However, in the postoperative test, rapid turnover proteins used as nutritional markers, such as, transthyretin, transferrin, and retinol binding protein, were more highly retained in the ghrelin group than in the placebo group. This finding is consistent with the findings in previous studies that ghrelin prevented nutritional deterioration. Furthermore, the time required to attain positive nitrogen balance was significantly shorter in the ghrelin group than in the placebo group (2.6±1.6 vs 4.3±1.8 days, respectively; P=0.0035; FIG. 4). We compared changes in weight and body composition between the 2 groups. During the study period, changes in body weight were monitored as a percentage of the weight on admission (preoperation). A comparison of body weight and body composition measured preoperatively and on POD10 showed that the percent decrease in total weight was −3.5±2.7% in the ghrelin group and −5.4±4.4% in the placebo group (P=0.32). Body composition analysis using dual-energy X-ray absorptiometry showed that the percent decrease in body fat weight in the ghrelin group (−3.2±5.0%) was similar to that in the placebo group (−3.6±4.6%; P=0.93). Similarly, the percent decrease in lean body weight in the ghrelin group (−4.2%±3.0%) was comparable to that in the placebo group (−6.0%±5.5%; P=0.11).

While several example embodiments of the invention have been described, it should be understood that the scope of the present invention is not limited to the described examples. Those skilled in the art will appreciate that various modifications may be made to the various embodiments of the invention without departing from the scope of the present invention. Thus, the present invention should be understood to cover all modifications that may fall within the scope of the appended claims.

REFERENCES

1. Enzinger P C, Mayer R J. Esophageal cancer. N Engl J Med. 2003; 349:2241-2252.
2. Sjoquist K M, Burmeister B H, Smithers B M, et al. Survival after neoadjuvant chemotherapy or chemoradiotherapy for resectable oesophageal carcinoma: an updated meta-analysis. Lancet Oncol. 2011; 12:681-692.
3. Kawahara Y, Ninomiya I, Fujimura T, et al. Prospective randomized controlled study on the effects of perioperative administration of a neutrophil elastase inhibitor to patients undergoing video-assisted thoracoscopic surgery for thoracic esophageal cancer. Dis Esophagus. 2010; 23:329-339.
4. Morita M, Yoshida R, Ikeda K, et al. Acute lung injury following an esophagectomy for esophageal cancer, with special reference to the clinical factors and cytokine levels of peripheral blood and pleural drainage fluid. Dis Esophagus. 2008; 21:30-36.
5. Derogar M, Orsini N, Sadr-Azodi O, et al. Influence of major postoperative complications on health-related quality of life among long-term survivors of esophageal cancer surgery. J Clin Oncol. 2012; 30:1615-1619.
6. Hirai T, Yamashita Y, Mukaida H, et al. Poor prognosis in esophageal cancer patients with postoperative complications. Surg Today. 1998; 28:576-579.
7. Opal S M, Fisher C J, Jr, Dhainaut J F, et al. Confirmatory interleukin-1 receptor antagonist trial in severe sepsis: a phase III, randomized, double-blind, placebocontrolled, multicenter trial. The Interleukin-1 Receptor Antagonist Sepsis Investigator Group. Crit Care Med. 1997; 25:1115-1124.
8. Akamoto S, Okano K, Sano T, et al. Neutrophil elastase inhibitor (sivelestat) preserves antitumor immunity and reduces the inflammatory mediators associated with major surgery. Surg Today. 2007; 37:359-365.
9. Ryugo M, Sawa Y, Takano H, et al. Effect of a polymorphonuclear elastase inhibitor (sivelestat sodium) on acute lung injury after cardiopulmonary bypass: findings of a double-blind randomized study. Surg Today. 2006; 36:321-326.
10. Sato A, Kuwabara Y, Shinoda N, et al. Use of low dose dopamine, gabexate mesilate and ulinastatin reduces thewater balance and pulmonary complication in thoracic esophagectomy patients. Dis Esophagus. 2005; 18:151-154.
11. Ono S, Aosasa S, Mochizuki H. Effects of a protease inhibitor on reduction of surgical stress in esophagectomy. Am J Surg. 1999; 177:78-82.
12. Sato N, Koeda K, Ikeda K, et al. Randomized study of the benefits of preoperative corticosteroid administration on the postoperative morbidity and cytokine response in patients undergoing surgery for esophageal cancer. Ann Surg. 2002; 236:184-190.
13. Shimada H, Ochiai T, Okazumi S, et al. Clinical benefits of steroid therapy on surgical stress in patients with esophageal cancer. Surgery. 2000; 128:791-798.
14. Tsukada K, Miyazaki T, Katoh H, et al. Effect of perioperative steroid therapy on the postoperative course of patients with oesophageal cancer. Dig Liver Dis. 2006; 38:240-244.
15. Shintani M, Ogawa Y, Ebihara K, et al. Ghrelin, an endogenous growth hormone secretagogue, is a novel orexigenic peptide that antagonizes leptin action through the activation of hypothalamic neuropeptide Y/Y1 receptor pathway. Diabetes. 2001; 50:227-232.
16. Masuda Y, Tanaka T, Inomata N, et al. Ghrelin stimulates gastric acid secretion and motility in rats. Biochem Biophys Res Commun 2000; 276:905-908.
17. Nagaya N, Moriya J, Yasumura Y, et al. Effects of ghrelin administration on left ventricular function, exercise capacity, and muscle wasting in patients with chronic heart failure. Circulation. 2004; 110:3674-3679.
18. Nagaya N, Itoh T, Murakami S, et al. Treatment of cachexia with ghrelin in patients with COPD. Chest. 2005; 128:1187-1193.
19. Strasser F, Lutz T A, Maeder M T, et al. Safety, tolerability and pharmacokinetics of intravenous ghrelin for cancer-related anorexia/cachexia: a randomised, placebo-controlled, double-blind, double-crossover study. Br J Cancer. 2008; 98:300-308.
20. Adachi S, Takiguchi S, Okada K, et al. Effects of ghrelin administration after total gastrectomy: a prospective, randomized, placebo-controlled phase II study. Gastroenterology. 2010; 138:1312-1320.
21. Yamamoto K, Takiguchi S, Miyata H, et al. Randomized phase II study of clinical effects of ghrelin after esophagectomy with gastric tube reconstruction. Surgery. 2010; 148:31-38.
22. Hiura Y, Takiguchi S, Yamamoto K, et al. Effects of ghrelin administration during chemotherapy with advanced esophageal cancer patients: a prospective, randomized, placebo-controlled phase 2 study. Cancer. 2012; 118:4785-4794.
23. Wu R, Dong W, Zhou M, et al. Ghrelin attenuates sepsis-induced acute lung injury and mortality in rats. Am J Respir Crit Care Med. 2007; 176:805-813.
24. Doki Y, Takachi K, Ishikawa 0, et al. Ghrelin reduction after esophageal substitution and its correlation to postoperative body weight loss in esophageal cancer patients. Surgery. 2006; 139:797-805.
25. Yamamoto K, Takiguchi S, Miyata H, et al. Reduced plasma ghrelin levels on day 1 after esophagectomy: a new predictor of prolonged systemic inflammatory response syndrome. Surg Today. 2013; 43:48-54
26. Tomimaru Y, Yano M, Takachi K, et al. Factors affecting the prognosis of patients with esophageal cancer undergoing salvage surgery after definitive chemoradiotherapy. J Surg Oncol. 2006; 93:422-428.
27. Sobin L H, Gospodawowics M K, Wittekind C H, eds. TNM Classification of Malignant Tumors, 7th edition. New York, N.Y.: Wiley-Liss, Inc 2009.
28. Ando N, Kato H, Igaki H, et al. A randomized trial comparing postoperative adjuvant chemotherapy with cisplatin and 5-fluorouracil versus preoperative chemotherapy for localized advanced squamous cell carcinoma of the thoracic esophagus (JCOG9907). Ann Surg Oncol. 2012; 19:68-74.
29. Osugi H, Takemura M, Higashino M, et al. Videoassisted thoracoscopic esophagectomy and radical lymph node dissection for esophageal cancer, et al. A series of 75 cases. Surg Endosc. 2002; 16:1588-1593.
30. Shiozaki H, Yano M, Tsujinaka T, et al. Lymph node metastasis along the recurrent nerve chain is an indication for cervical lymph node dissection in thoracic esophageal cancer. Dis Esophagus. 2001; 14:191-196.
31. Yamasaki M, Miyata H, Fujiwara Y, et al. Minimally invasive esophagectomy for esophageal cancer: comparative analysis of open and hand-assisted laparoscopic abdominal lymphadenectomy with gastric conduit reconstruction. J Surg Oncol. 2011; 104:623-628.
32. Muckart D J, Bhagwanjee S. American College of Chest Physicians/Society of Critical Care Medicine Consensus Conference definitions of the systemic inflammatory response syndrome and allied disorders in relation to critically injured patients. Crit Care Med. 1997; 25:1789-1795.
33. Dindo D, Demartines N, Clavien P A. Classification of surgical complications: a new proposal with evaluation in a cohort of 6336 patients and results of a survey. Ann Surg. 2004; 240:205-213.
34. Akamizu T, Shinomiya T, Irako T, et al. Separate measurement of plasma levels of acylated and desacyl ghrelin in healthy subjects using a new direct ELISA assay. J Clin Endocrinol Metab. 2005; 90:6-9.
35. Mazess R B, Barden H S, Bisek J P, et al. Dual-energy x-ray absorptiometry for total-body and regional bonemineral and soft-tissue composition. Am J Clin Nutr. 1990; 51:1106-1112.

36. Shimakawa T, Naritaka Y, Asaka S, et al. Neoadjuvant chemotherapy (FAP) for advanced esophageal cancer. Anticancer Res. 2008; 28:2321-2326.
37. Yamasaki M, Miyata H, Tanaka K, et al. Multicenter phase I/II study of docetaxel, cisplatin and fluorouracil combination chemotherapy in patients with advanced or recurrent squamous cell carcinoma of the esophagus. Oncology. 2011; 80:307-313.
38. Daly J M, Fry W A, Little A G, et al. Esophageal cancer: results of an American College of Surgeons Patient Care Evaluation Study. J Am Coll Surg. 2000; 190:562-572, discussion 572-573.
39. Viklund P, Lindblad M, Lu M, et al. Risk factors for complications after esophageal cancer resection: a prospective population-based study in Sweden. Ann Surg. 2006; 243:204-211.
40. Sakamoto K, Arakawa H, Mita S, et al. Elevation of circulating interleukin 6 after surgery: factors influencing the serum level. Cytokine. 1994; 6:181-186.
41. Sato N, Koeda K, Kimura Y, et al. Cytokine profile of serum and bronchoalveolar lavage fluids following thoracic esophageal cancer surgery. Eur Surg Res. 2001; 33:279-284.
42. Li W G, Gavrila D, Liu X, et al. Ghrelin inhibits proinflammatory responses and nuclear factor-kappaB activation in human endothelial cells. Circulation. 2004; 109:2221-2226.
43. Liu X, Xiao Q, Zhao K, et al. Ghrelin inhibits high glucose-induced PC12 cell apoptosis by regulating TLR4/NF-kappaB pathway. Inflammation. 2013; 36: 1286-1294
44. Xu X, Jhun B S, Ha C H, et al. Molecular mechanisms of ghrelin-mediated endothelial nitric oxide synthase activation. Endocrinology. 2008; 149:4183-4192.
45. Konturek P C, Brzozowski T, Engel M, et al. Ghrelin ameliorates colonic inflammation. Role of nitric oxide and sensory nerves. J Physiol Pharmacol. 2009; 60:41-47.
46. Wang W, Bansal S, Falk S, et al. Ghrelin protects mice against endotoxemia induced acute kidney injury. Am J Physiol Renal Physiol. 2009; 297:F1032-F1037.
47. Wu R, Dong W, Zhou M, et al. Ghrelin improves tissue perfusion in severe sepsis via downregulation of endothelin-1. Cardiovasc Res. 2005; 68:318-326.
48. Li Y, Hai J, Li L, et al. Administration of ghrelin improves inflammation, oxidative stress, and apoptosis during and after nonalcoholic fatty liver disease development. Endocrine. 2013; 43:376-386.
49. ZhangH, Cui Z, LuoG, et al. Ghrelin attenuates intestinal ischemia/reperfusion injury in mice by activating the mTOR signaling pathway. Int J Mol Med. 2013; 32:851-859.
50. Vila G, Maier C, Riedl M, et al. Bacterial endotoxin induces biphasic changes in plasma ghrelin in healthy humans. J Clin Endocrinol Metab. 2007; 92:3930-3934.
51. Koch A, Sanson E, HelmA, et al. Regulation and prognostic relevance of serum ghrelin concentrations in critical illness and sepsis. Crit Care. 2010; 14:R94.
52. Miki K, Maekura R, Nagaya N, et al. Ghrelin treatment of cachectic patients with chronic obstructive pulmonary disease: a multicenter, randomized, double-blind, placebo-controlled trial. PLoS One. 2012; 7:e35708.
53. Kodama T, Ashitani J, Matsumoto N, et al. Ghrelin treatment suppresses neutrophil-dominant inflammation in airways of patients with chronic respiratory infection. Pulm Pharmacol Ther. 2008; 21:774-779.

What is claimed is:

1. A method for reducing the incidence of postoperative pulmonary complications in a surgical patient after an esophagectomy, the method comprising:
   administering an effective amount of ghrelin to the surgical patient perioperatively, beginning at a time 1 day prior to and up to 7 days after the esophagectomy.
2. The method according to claim 1, wherein the postoperative pulmonary complication is pneumonia.
3. The method according to claim 1, wherein the ghrelin is administered to the surgical patient continuously at an effective dosage.
4. The method according to claim 3, wherein the ghrelin is administered to the surgical patient for a period of from 5 to 7 days perioperatively.
5. The method according to claim 3, wherein the ghrelin is administered at a dosage of from 0.1 to 2.0 µg/kg/h.
6. The method according to claim 3, wherein the ghrelin is administered at a dosage of from 0.3 to 0.7 µg/kg/h.
7. The method according to claim 1, wherein the ghrelin is administered intravenously.
8. The method according to claim 7, wherein the ghrelin is administered via a central vein or a peripheral vein.
9. The method according to claim 8, wherein the ghrelin is administered via a subclavian vein.
10. The method according to claim 1, further comprising administering a steroid composition to the surgical patient perioperatively.
11. The method according to claim 10, wherein the steroid composition includes methylprednisolone.
12. The method according to claim 9, wherein the dosage of methylprednisolone is 10 mg/kg body weight or 250 mg per body.
13. A method of treating or preventing postoperative pulmonary complications in a surgical patient after an esophagectomy, the method comprising:
   administering an effective amount of ghrelin to the surgical patient perioperatively, beginning at a time 1 day prior to and up to 7 days after the esophagectomy.
14. The method according to claim 13, wherein the postoperative pulmonary complication occurs in a lung that is deflated during the esophagectomy.
15. The method according to claim 13, wherein the postoperative pulmonary complication is due to one-lung ventilation.
16. The method according to claim 13, wherein the ghrelin is administered to the surgical patient continuously at an effective dosage.
17. The method according to claim 16, wherein the ghrelin is administered at a dosage of from 0.1 to 2.0 µg/kg/h.
18. The method according to claim 16, wherein the ghrelin is administered to the surgical patient for a period of from 5 to 7 days perioperatively.
19. The method according to claim 13, wherein the ghrelin is administered intravenously via a central vein or a peripheral vein.
20. A method for preventing and controlling postoperative pulmonary complications in a surgical patient after an esophagectomy, with or without one-lung ventilation, the method comprising:
   administering an effective amount of ghrelin to the surgical patient perioperatively, beginning at a time 1 day prior to and up to 7 days after the esophagectomy.

* * * * *